Ｕnited States Patent [19]

Yu et al.

[11] Patent Number: 5,969,127
[45] Date of Patent: Oct. 19, 1999

[54] 3' UNTRANSLATED REGIONS OF α-AMYLASE GENES

[75] Inventors: Su-May Yu; Ming-Tsair Chan, both of Taipei, Taiwan

[73] Assignee: Academia Sinica, Taiwan

[21] Appl. No.: 08/951,718

[22] Filed: Oct. 16, 1997

[51] Int. Cl.[6] ........................ C12N 15/29; C12N 15/82; C12N 15/84; A01H 4/00
[52] U.S. Cl. ................... 536/24.1; 536/24.2; 536/23.6; 435/70.1; 435/69.1; 435/468; 435/469; 435/204; 435/410; 435/419; 800/278; 800/287; 800/284; 800/320.2
[58] Field of Search .................. 536/23.6, 24.1, 536/24.2; 435/419, 70.1, 69.1, 468, 469, 204, 410; 800/205, 200, DIG. 57, 278, 287, 284, 320.2

[56] References Cited

U.S. PATENT DOCUMENTS 5,460,952  10/1995  Yu et al. .

OTHER PUBLICATIONS

Purvis et al. Nucleic Acid Research. 1987. vol. 15:7951–7962, 1987.
Kim et al. Plant Molecular Biology. 1994. vol.24: 105–117.
Dekeyser et al. The Plant Cell. 1990. vol. 2: 591–602.
Matzke and Matzke. Plant Physiol. 1995. vol. 107: 679–685.
Finnegan and McElory. 1994. Bio/Technology. 12: 883–888.
Cornejo et al. Plant Molecular Biology. 1993. vol. 23: 567–581.
O'Neill et al. Molecular and General Genetics. 1990. vol. 221: 235–244.
Chan et al. The journal of Biological Chemistry. 1994. vol. 269: 17635–17641.
Chen et al., "Expression of α–amylases, carbohydrate metabolism, and autophagy . . . ", The Plant Journal 6(5):625–636, 1994.
Gallie et al., "The Regulation of Gene Expression in Transformed Maize Aleurone and Endosperm Protoplasts", Plant Physiol. 106:929–939, 1994.
Gil et al., "Multiple Regions of the Arabidopsis SAUR–AC1 gene control transcript abundance . . . ", EMBO J. 15:1678–1686, 1996.
Gubler et al., "Gibberellin–responsive elements in the promoter . . . ", Plant Cell 4:1435–1441, 1992.
Lanahan et al., "A gibberellin response complex in cereal α–amylase gene promoters", Plant Cell 4:203–211, 1992.
Sheu et al., "Control of Transcription and mRNA turnover as mechanisms of metabolic . . . ", Plant J. 5:655–664, 1994.
Sheu et al. "Carbohydrate Starvation Stimulates Differential Expression of Rice . . . ", The Journal of Biochemistry 271(43):26998–27004, 1996.
Sijmons et al., "Production of Correctly Processed Human Serum Albumin in Transgenic Plants", Biotechnology 8:217–221, 1990.
Tanida et al., "Functional dissection of a rice high–pI α–amylase multigene . . . ", Mol. Gen. Genet. 244:127–134, 1994.

*Primary Examiner*—Gary Benzion
*Assistant Examiner*—Ousama M-Faiz Zaghmout
*Attorney, Agent, or Firm*—Fish & Richardson P.C.

[57] ABSTRACT

An expression vector comprising a promoter capable of directing expression of a coding sequence in an angiosperm cell, and a 3' untranslated region of a rice α-amylase gene, wherein, after the coding sequence is inserted into the vector, the 3' untranslated region and the coding sequence are transcribed into a single mRNA. Also featured are methods of producing a polypeptide in angiosperm cells using such a vector.

18 Claims, 4 Drawing Sheets

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 320 base pairs
       (B) TYPE: nucleic acid
       (C) STRANDEDNESS: single
       (D) TOPOLOGY: linear (xi) SEQUENCE DESCRIPTION: SEQ ID NO:1:

CGGGCTCAAG CCCTAAACTG AACGGGATAG TCATGCTCAA ACCAGTTTCT ACACGGCAAG      60

AATTTACTGA TTCTTATACT TTTGCAGTCA ATTAAATTAT GGTTTTTATA TATGTAATTT     120

TGTATCCGAT TGTAGCGTTC GAATAAGTAG GCAGGCTCTC TAGCCTCTAG GTTAATTGCG     180

GGGCATATGT AGCTTGCCAG TTAATTGTGT TTGTATCACG CAGTTTGTAA CCGTTGGTGC     240

ATATATATGT CAGGTTCAGG TTCAGGATGC AGTAAAAAAT CATACTGCAC CGATCAGTGA     300

GTTTTTATAT ACTGGTTTTA                                                 320

(2) INFORMATION FOR SEQ ID NO:2:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (xi) SEQUENCE DESCRIPTION: SEQ ID NO:2:

TAATCTAGAT AGCGGGCTCA AGCCCTA                                          27

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:3:

TCCCCGCGGT CAGTGAGTTT TTA                                              23

(2) INFORMATION FOR SEQ ID NO:4:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (xi) SEQUENCE DESCRIPTION: SEQ ID NO:4:

TATATAATGT CAGGTT                                                      16

(2) INFORMATION FOR SEQ ID NO:5:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:5:

-continued

TGCTCTAGAT AATTCTTCGA CCCA                              24

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

TCCCCGCGGT GGTACCCGCA TCA                               23

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

GCGGGACTCT SSTCATAAAA                                   20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

ACGGCATCAA CGCCGGGAGC                                   20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

CTGATGGACA GGTTATCACC                                   20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

TCAGCGATGA CGAAATTCTT                                   20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

TCTCTTTGAT GTGCTGTGCC                                   20

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

TGAGCTCGGC TCAAGCCCTA AA                                        22

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

TGAGCTCCTA CAATCGGATA CA                                        22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:14:

TGAGCTCTTG TATCCGATTG TA                                        22

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

TGAGCTCTGG CAAGCTACAT AT                                        22

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

TGAGCTCGGC ATATGTAGCT T                                         21

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGAGCTCCCT GAACCTGAAC CT                                        22

3' UNTRANSLATED REGIONS OF α-AMYLASE GENES

FIELD OF THE INVENTION

This invention relates to the field of gene expression regulation in plant cells.

BACKGROUND OF THE INVENTION

Sugar repression of gene expression is a ubiquitous regulatory mechanism for both prokaryotic and eukaryotic cells to adjust to changes in nutrient availability. In multicellular plants, expression of enzymes involved in carbohydrate metabolism is often feedback-regulated by sugar metabolites (Sheen, J., *Photosynth. Res.*, 39:427–438, 1994). For instance, carbohydrate depletion has been shown to enhance expression of a wide variety of genes involved in photosynthesis, reserve mobilization, and export processes (Koch, *Annu. Rev. Plant Physiol. Plant Mol. Biol.*, 47:509–540, 1996).

α-amylases are the major amylolytic enzymes for hydrolysis of starch stored in the endosperm during germination of cereal grains. These enzymes are encoded by a group of genes whose expression is repressed by sugars. In the embryos of germinating rice seeds, the transient expression of certain α-amylase genes is thought to be induced by sugar depletion in the embryos following imbibition of the seeds, and suppressed by sugar influx from the endosperm as germination proceeds (Yu et al., *Plant Mol. Biol.* 30:1277–1289, 1996). Similarly, expression of α-amylase genes in cultured rice suspension cells has also been shown to be suppressed by sugar present in the medium and induced in its absence (Yu et al., *J. Biol. Chem.*, 266:21131–21137, 1991, *Gene* 122:247–253 1992; Chen et al., *Plant J.*, 6:625–636, 1994). Further studies reveal that the transcription rate of α-amylase genes in rice suspension cells increases in response to sucrose depletion in the culture medium (Sheu et al., *Plant J.*, 5:655–664, 1994). Protein expression systems have been established to make use of the sugar-responsive promoters of these α-Amylase genes (U.S. Pat. No. 5,460,952 to Yu et al.).

Sugar-regulated stability of rice α-amylase mRNAs, on the other hand, has also been investigated. Under transcription-inhibiting conditions, the mRNA half-lives of three α-amylase genes were found to be prolonged by sucrose-starvation (Sheu et al., *J. Biol. Chem.*, 271:26998–27004, 1996). This result suggests that, in addition to enhanced transcription rate, increased mRNA stability may also contribute to the elevation of the steady-state levels of certain α-amylase mRNA species in sucrose-starved cells. It is unclear, however, what mechanism is responsible for the increased degradation of α-amylase mRNAs in cells provided with sucrose as compared to cells deprived of sucrose. It has been postulated that mRNA transcripts are selected for degradation in a sequence-dependent manner (Sachs, *Cell,* 74:413–421, 1993). Yet it remains largely unknown what sequences in RNA transcripts are responsible for targeting degradation in plants.

SUMMARY OF THE INVENTION

The invention is based on the discovery that the 3' untranslated regions of a rice α-amylase gene can cis-regulate mRNA stability in angiosperm cells in a sugar-responsive manner.

Accordingly, the invention features expression vectors that comprise (i) a promoter capable of directing expression of a coding sequence in an angiosperm cell; and (ii) a 3' untranslated region (3'UTR) of a rice α-amylase gene (i.e., a sequence that is identical to a given 3'UTR of a rice α-amylase gene, or a functional variant of the given 3'UTR). In these vectors, the 3'UTR is no longer linked to an α-amylase coding sequence as in its cognate α-amylase gene or a cDNA obtained therefrom. After a coding sequence (e.g., a non-α-amylase coding sequence) is inserted into the vectors, the coding sequence and the 3'UTR are transcribed into a single ribonuleic acid, e.g., messenger ribonucleic acid (mRNA). An angiosperm cell is a monocotyledon, such as cereal (e.g., rice, barley, and wheat), or dicotyledon cell.

The promoter in the expression vectors can be a ubiquitously active one, such as one that is derived from an actin gene, cauliflower mosaic virus 35S ("CaMV35S") RNA or a ubiquitin gene, or an inducible one, such as one that is derived from an α-amylase (e.g., the rice αAmy3, αAmy6, αAmy7, αAmy8, or αAmy10 gene, which are also sugar-responsive); see U.S. Pat. No. 5,460,952), invertase, sucrose synthase, patatin, β-amylase, or sporamin gene. Other appropriate transcription regulatory elements such as enhancers can also be included in the vectors.

If the α-amylase 3'UTR is used to stabilize mRNA in the absence or low concentration of sugars, the sugar-suppressible promoters, such as the photosynthetic gene and α-amylase gene promoters can be used.

The coding sequence can encode, for example, a polypeptide, or an antisense RNA that interferes with the function of another RNA (e.g., mRNA, transfer RNA, ribosomal RNA, and small nucleolar RNA).

The 3' untranslated region is typically selected for its ability to cis-regulate RNA stability in a sugar-responsive manner. The 3' untranslated region can be derived from, for example, a 3' untranslated region (3'UTR) of a rice α-amylase 3 (αAmy3) gene, i.e., an αAmy3 gene of any rice strain; that is, the 3'UTR of the vectors can be identical to, or a functional variant (e.g., containing one or more silent mutations) of, a rice αAmy3 3'UTR. The 3'UTR can be obtained either by chemical synthesis or recombinant technology. The 3'UTRs include, but are not limited to, sequences consisting of 20 or more consecutive nucleotides from SEQ ID NO:1, e.g., sequences spanning nucleotides 44–320, 44–75, 75–320, 75–124, 124–320, 124–154, 154–320, 154–184, 184–320, 184–237, 237–320, 237–258, 258–320, 3–135, 119–199, and 182–276 of SEQ ID NO:1. The 3'UTR can be in either correct or reverse orientation in relation to the promoter's direction.

The expression vectors can further comprise a signal-peptide-encoding sequence (e.g., one that is derived from a rice α-amylase gene) downstream of the promoter, so that the polypeptide products expressed from the expression vectors can be secreted by host cells.

To facilitate cloning, the expression vectors of the invention may comprise multiple restriction sites downstream of the promoter so that a coding sequence can be conveniently inserted into the vector between the promoter and the rice 3'UTR.

The invention also features methods of producing a polypeptide in angiosperm cells. These methods utilize an expression construct containing a coding sequence for a polypeptide of interest, linked operably to a promoter capable of directing its expression in an angiosperm cell, and a 3' untranslated region of a rice α-amylase gene. The coding sequence and the untranslated region are not naturally transcribed into a single mRNA, but are so in the construct Such a construct is also within the scope of the invention.

In a method of the invention, appropriate angiosperm host cells are first transformed by the expression construct, and the transformed cells (including cells derived therefrom, e.g., through replication, regeneration, or differentiation) are then subjected to a sugar-free, or sugar-containing, environment to promote expression of the polypeptide. If the 3'UTR contained in the expression construct enhances mRNA stability when the host cells are placed in a medium or environment containing sugar (at, e.g., 1 mM to 300 mM), then the transformants are subjected to such a medium or environment to promote expression of the polypeptide; examples of such a 3'UTR include, but are not limited to, sequences spanning nucleotides 119–199, 124–320, 154–320, and 258–320 of SEQ ID NO:1. On the other hand, if the 3'UTR enhances mRNA stability when the host cells are placed in a sugar-free environment, the transformants can be placed in such an environment to promote the polypeptide's production; examples of such a 3'UTR include, but are not limited to SEQ ID NO:1, sequences spanning nucleotides 3–135, 44–320, 75–320, 184–320, 237–320, and 182–276 of SEQ ID NO:1. A sugar can be sucrose, glucose, fructose, maltose, or any polysaccharide as long as it is metabolizable and provides a carbon source for cells.

A sugar-free (i.e., sugar-starved) environment refers to an environment, e.g., a culture medium, that does not contain any sugar, or an environment whose sugar concentration is so low that it does not support the proliferation or respiration of cells. Occurrence of sugar starvation depends on multiple factors such as sugar concentration, the cell-to-medium volume ratio, and the length of incubation time in a medium.

Of course, the above transformants can also be regenerated to tissue or even a whole plant (i.e., a transgenic plant) to promote expression of the polypeptide. Seeds of such a transgenic plant may also be germinated to promote expression of the recombinant polypeptide.

To further promote expression of the polypeptide, the promoter in the expression construct can be sugar-responsive in synergy with the 3'UTR. For instance, if the 3'UTR enhances mRNA stability in the absence of sugar, then a promoter that is activated by sugar starvation (e.g., a promoter derived from a rice αAmy3, αAmy6, αAmy7, αAmy8, and αAmy10 gene) can be employed in the expression construct. By way of example, a coding sequence in association with an αAmy3 promoter and the full length αAmy3 3'UTR is highly expressed in sugar-starved cells.

To facilitate recovery of the expressed polypeptide, a signal-peptide-encoding sequence can be integrated into the expression construct at an appropriate position, e.g., between the promoter and a coding sequence for the polypeptide. As a result, the polypeptide can be secreted to the culture medium, and thereby conveniently recovered.

Other features and advantages of the invention will be apparent from the following detailed description, and from the claims.

DETAILED DESCRIPTION

Figure 1:
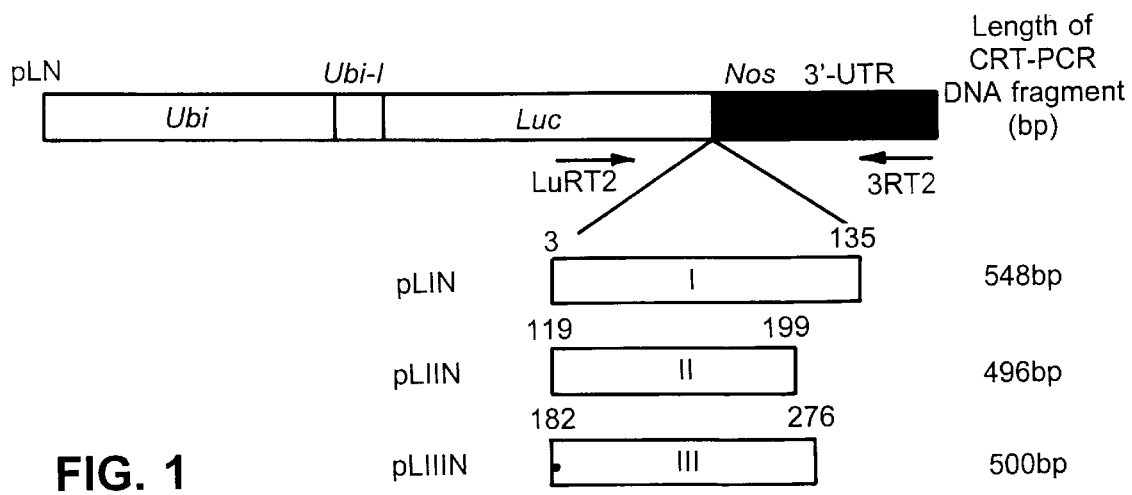
FIG. 1 is a set of schematic diagrams showing the various plasmid constructs used for rice transformation. Positions of primers (arrowheads; for sequences, see Table 1) for CRT-PCR and expected lengths of PCR products are also shown. All the constructs contain the maize ubiquitin (Ubi) promoter, the Ubi first intron (Ubi-I), the luciferase (Luc) or β-glucuronidase (Gus) coding sequence, and a 3' UTR of αAmy3, Agrobacterium nopaline synthase (Nos), or actin 1 (Act1) gene. Fragments (or subdomains) I, II, and III derived from the various regions of the full-length αAmy3 3'UTR were inserted into pLN between the Luc coding region and the Nos 3'UTR. The nucleotide sequences are numbered from the first nucleotide after the translation stop codon TGA.
Figure 1:
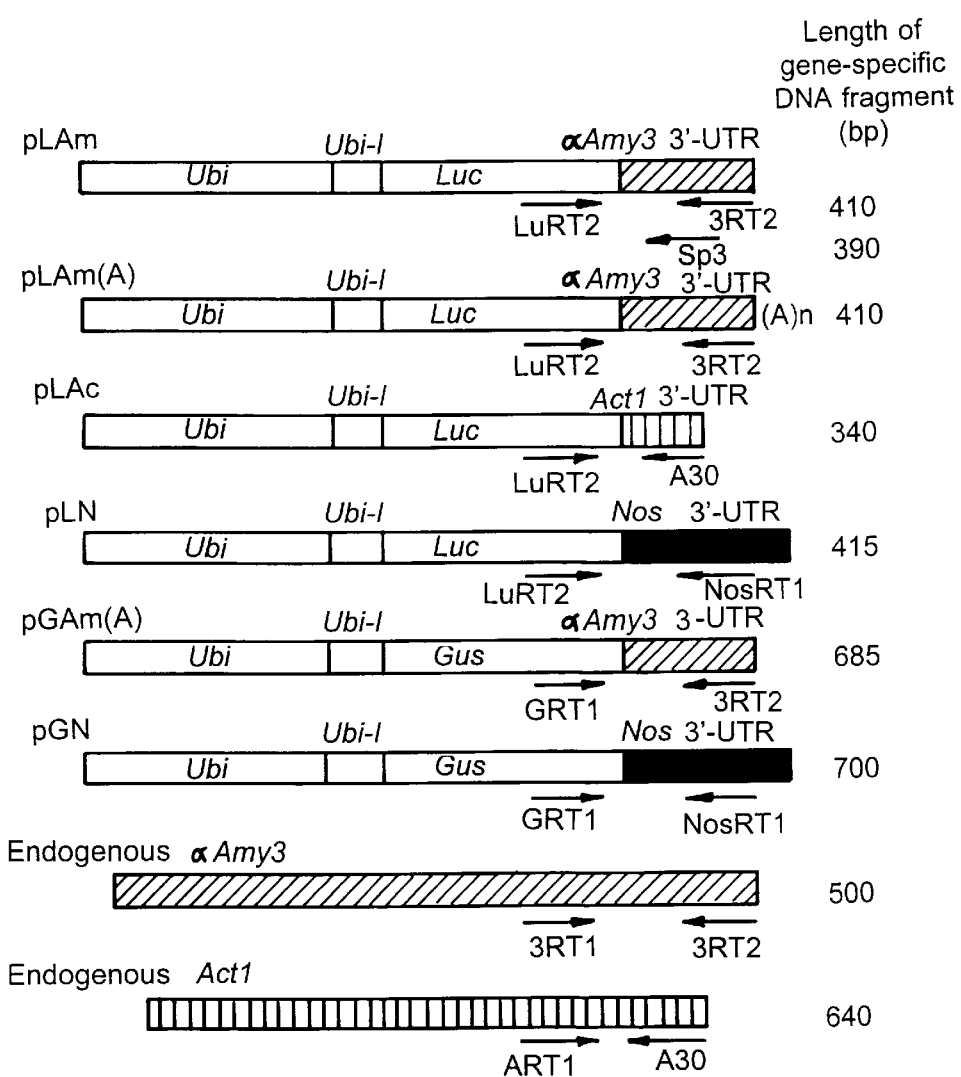

Described below is the discovery that the full-length 3' untranslated region (SEQ ID NO:1) of a rice α-amylase gene (αAmy3) enhances mRNA stability in the absence of sugar (e.g., sucrose and glucose), and promotes mRNA degradation in the presence of sugar; and that fragments of the full-length αAmy3 3' untranslated region (3'UTR) can independently regulate mRNA accumulation in a sugar-responsive manner.

The expression vectors of the invention, which contain a 3'UTR of a rice α-amylase gene, can be generated by standard recombinant technology (see, e.g., Sambrook et al., *Molecular Cloning, A Laboratory Manual*, 2nd Ed., Cold Spring Harbor Press, Cold Spring Harbor, N.Y., 1989; and Ausubel et al., *Current Protocols in Molecular Biology*, Greene Publishing and Wiley-Interscience, New York, N.Y., 1993). For instance, a DNA fragment containing the 3'UTR is first obtained by polymerase chain reaction, using a rice α-amylase cDNA as a template, and then inserted into a plasmid that has already had an appropriate angiosperm promoter (or additionally, a coding sequence downstream of the promoter) in place.

Plant cells can be transfected with the expression vectors using standard methods, such as electroporation, particle bombardment, microinjection, ultrasonic method, polyethylene glycol-mediated protoplast transformation, poly-L ornithine method, calcium phosphate method, and Agrobacterium-mediated transformation system (see, e.g., U.S. Pat. No. 5,460,952, columns 17–18; and references in the patent).

Plant cells transformed by expression constructs (i.e., expression vectors containing a sequence encoding, e.g., a desired polypeptide) can be maintained and expanded in a sugar-free or sugar-containing culture medium to promote expression of the polypeptide. The polypeptide can be subsequently extracted and purified from the cells using standard techniques. Alternatively, the polypeptide can be isolated from the culture medium if the expression constructs contain a signal peptide-encoding sequence so that the polypeptide is secreted into the medium (Chen et al., *Plant J.*, 6:625–638, 1994; Sijmons et al., *Bio/Technology*, 8:217–221, 1990). One advantage of purifying proteins directly from a culture medium is that the amount of contaminant protein is substantially lower in culture media than in cell extracts.

Transformed plant cells can also be regenerated to transgenic tissue or a transgenic plant by well known techniques (see, e.g., Datta et al., Bio/Technology, 8:736–740, 1990; Peng et al., Plant Cell Reports, 9:168–172, 1990; Yang et al., Plant Cell Reports, 7:421–425, 1988; U.S. patent applications Ser. No. 08/509,962 and 08/639,792). The recombinant polypeptide can then be recovered from the transgenic tissue or plant (or a part of the plant, such as its leaves, sheaths, stems, seeds, and roots, depending on the tissue-specificity of the promoter used). Both photosynthetic leaves and the endosperm of germinating seeds provide high amounts of sugar; thus, recombinant polypeptides can be harvested from these tissues if the polypeptide expression vectors contain 3'UTRs that stabilize mRNAs in a sugar-containing environment.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, exemplary methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following data and protocols are used as examples to illustrate, but not limit, the expression vectors, constructs, and methods of the invention.

EXAMPLE 1

This example concerns the sugar-regulated stability of an αAmy3 mRNA. Studies disclosed in this example demonstrate that the full-length αAmy3 3'UTR and two of its three subdomains, i.e., subdomains I and III, function as destabilizing determinants in mRNA turnover in the presence of sugars.

Plant Materials

The rice variety used for transformation was Oryzae sativa L. cv. Tainan 5. Embryogenic calli were initiated as described by (Chan et al. Plant Mol. Biol., 22:491–506, 1993), except that the medium was replaced with MS medium (Murashige, Physiol. Plant, 15:473–497, 1962) containing 1% agarose (w/v), 3% sucrose, and 2 µg/ml 2,4-Dichlorophenoxyacetic acid ("2,4-D"; pH 5.8). After four weeks, suspension cultures were initiated by transferring the calli into a liquid MS medium containing 3% sucrose, 2 µg/ml 2,4-D, 0.2 µg/ml kinetin, and 0.1 µg/ml $GA_3$. The suspension culture was shaken on a reciprocal shaker at 120 rpm and incubated at 26° C. in the dark. Suspension cells were subcultured weekly prior to bombardment.

Transformation of rice suspension cells

In a volume of 70 µl, 1.5 mg of gold particles (Bio-Rad) with an average size of 1 µm in diameter were coated with 2 µg of test plasmid and 1 µg of pTRA151 (a plasmid containing hygromycin resistant gene (Zheng, et al., Plant Physiol., 97:832–835, 1991) by a $CaCl_2$/spermidine precipitation method (Cao et al., Plant Gene Transfer, eds. Lamb, C. J. & Beachy, R. N., Wiley-Liss, New York, pp. 21–33, 1990). Rice suspension cells were bombarded with the coated gold particles as described by Cao et al. (Plant Cell Rep., 11:586–591., 1992) using a helium gas retrofitted BIOLISTIC™PDS-1000 Particle Delivery System (Bio-Rad). Bombarded cells were transferred to fresh MS solid medium and incubated at 26° C. in the dark for 6 days before being transferred to MS solid medium containing 50 µg/ml hygromycin. After 4 weeks, all putative transformed calli were subcultured to MS liquid medium containing 50 µg/ml hygromycin to generate suspension cell culture.

Determination of mRNA half life

Transgenic cells were cultured in suspension in sucrose-containing (+S) medium for 96 h and transferred to sucrose-free (-S) medium for 24 h. Actinomycin D (ActD) was then added to the medium to a final concentration of 10 µg/ml. Cells were incubated for another 12 hours (h) and then divided into two halves. One half of the cells were transferred to a +S medium containing ActD, while the other half of cells were transferred to a -S medium containing ActD. Cells were harvested after 0.5 to 9 h, and total cellular RNAs were extracted, electrophoresed on polyacrylamide gel, and transferred to a nylon membrane. Northern blot analysis of the RNAs was performed using a radioactive probe that hybridized to the luciferase gene (Luc) sequence. Radioactive signals were quantified using a PhosphoImager. The mRNA level in each lane was normalized to the rRNA level (obtained using an rRNA probe). The logarithm values of mRNA levels were subjected to linear regression analysis and plotted as a function of time.

Results (1) The Full-Length αAmy3 3'UTR and Certain Subdomains Thereof Mediate Sugar-Dependent Repression of mRNA Accumulation Effects of an αAmy3 3'UTR on the accumulation of a heterologous mRNA were investigated in transgenic rice cell lines. Used for transformation were plasmids pLAm and pLN (see Example 2, infra), which contained (i) the full-length αAmy3 3'UTR, and (ii) the Agrobacterium nopaline synthase gene (Nos) 3'UTR, respectively, downstream from the ubiquitin (Ubi) promoter and the Luc coding region. Also used were plasmids pLIN, pLIIN, and pLIIIN (see Example 2, infra), which respectively contained fragments I, II, and III of the full-length αAmy3 3'UTR between the Luc coding region and the Nos 3'UTR. Schematic structures of these plasmids are shown in FIG. 1. Identification of transgenic rice calli was confirmed by Southern analysis of genomic DNA.

Figure 2:
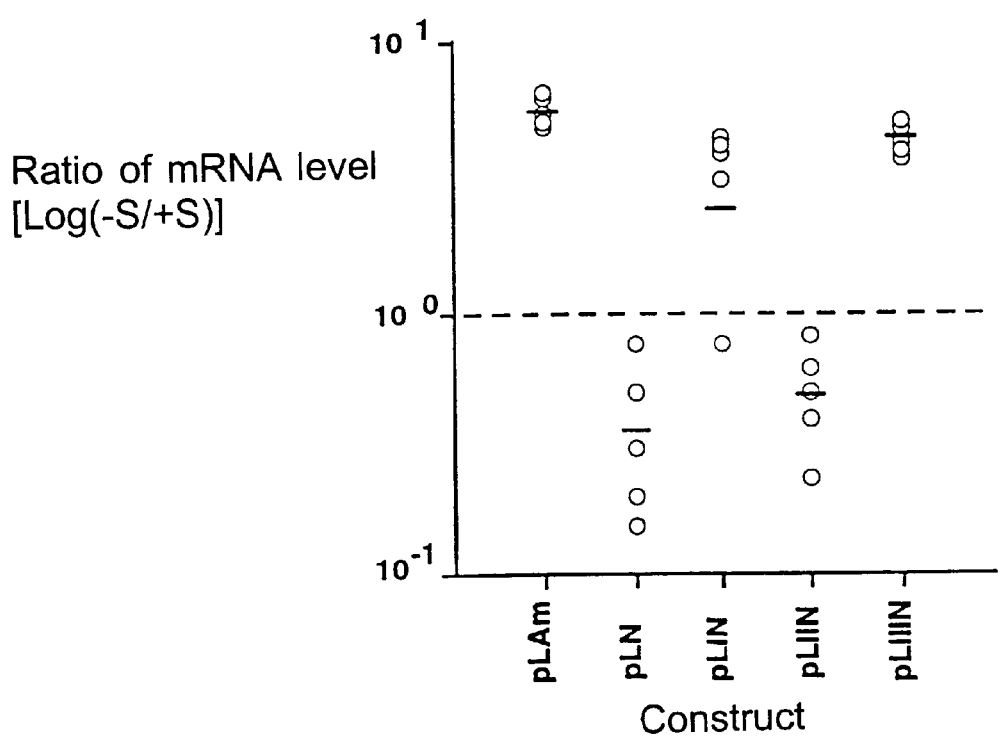
FIG. 2 is a graph showing that the full-length αAmy3 3'UTR and three fragments thereof mediate sugar-dependent decrease or increase of heterologous mRNA accumulation in transgenic rice suspension cells.

Five independently-transformed cell lines were randomly selected for each plasmid construct, and levels of the Luc mRNA were examined by RNA dot blot analysis using a segment derived from the Luc coding sequence as a probe (FIG. 2). Radioactive signals generated by the hybridized Luc mRNA in each dot were quantified using a Phospho-Imager (Molecular Dynamics). The ratio of mRNA levels in the absence (-S) versus presence (+S) of sucrose was determined for each transformed cell line. Logarithm value of each ratio (open circle) was then used to plot the graph. Bold horizontal bars represent the average value for each construct. A ratio higher than $log10^0$ (i.e., 1) indicates that the Luc mRNA level was increased by sucrose starvation, whereas a ratio lower than $log10^0$ indicates the Luc mRNA level was decreased by sucrose starvation.

FIG. 2 shows that the Luc mRNA levels in cell lines transformed with pLAm, pLIN, and pLIIIN were increased by sucrose starvation; in contrast, the Luc mRNA levels in cell lines transformed with pLN and pLIIN were decreased by sucrose starvation. In all the cell lines tested, levels of the endogenous αAmy3 mRNA were increased, while levels of the endogenous actin (Act) MRNA were decreased, by sucrose starvation.

The above results were consistent with those of the transient assays in rice protoplasts (Example 2, infra): The full-length αAmy3 3'UTR and at least two of its different subdomains specifically mediate sugar-dependent decrease of the accumulation of the Luc-Nos mRNA (i.e., mRNA containing the Luc coding sequence and the Nos 3'UTR) whose accumulation otherwise is increased by sugar provision. Of note, in the presence of sucrose, levels of the Luc mRNA in cells transformed with pLAm, pLIN, and pLIIIN were still detectable, while those of the endogenous αAmy3 MRNA were not. This was probably due to a higher transcriptional activity of the Ubi promoter than the αAmy3 promoter in sucrose-provided cells.

(2) The Full-Length αAmy3 3'UTR Functions as a Sugar-Responsive mRNA Stability Determinant To determine whether the low accumulation of the αAmy3 3'UTR-containing chimeric mRNAs in sucrose-provided cells was due to their rapid turnover, the half-lives of the chimeric mRNAs were measured by shutting off transcription of the pLAm-transformed cells. Half-lives of mRNAs were determined by Northern analysis following transcription inhibition by ActD (Sheu, et al., *Plant J.*, 5:655–664, 1994).

Levels of the Luc-αAmy3 (i.e., mRNAs containing the Luc coding sequence and an αAmy3 3'UTR) and endogenous αAmy3 mRNAs were low or undetectable in cells provided with sucrose, but increased significantly after cells were sucrose-starved for 24, 36, or 45 h. The Luc-αAmy3 and αAmy3 mRNAs that accumulated after cells had been starved for 24 h and then treated with ActD for 12 h decayed slowly in cells subsequently starved for sucrose, but decayed rapidly in cells subsequently provided with sucrose. In contrast, the levels of actin mRNA were high in cells provided with sucrose, but were low in cells starved for sucrose or provided with ActD.

The relative half-lives of Luc-αAmy3 and αAmy3 mRNAs were both found to be 70 minute (min) in cells provided with sucrose. The half-lives increased to 300 and 320 min, respectively, when the cells were starved for sucrose. These results demonstrate that the Luc mRNA carrying the full-length αAmy3 3'UTR is more stable in cells starved for sucrose.

(3) Various Subdomains of the Full-Length αAmy3 3'UTR Act Independently as Sugar-Responsive mRNA Stability Determinants Since insertion of subdomains I or III of the full-length αAmy3 3'UTR between the Luc coding region and the Nos 3'UTR conferred sugar-dependent decrease of mRNA accumulation (FIG. 2), we sought to determine whether the two subdomains confer differential stability to the heterologous mRNA. The turnover of mRNAs in transgenic rice suspension cells was determined by Northern analysis following transcription inhibition by ActD. In the pLN- and pLIIN-transformed cells, the Luc-Nos and Luc-II-Nos (i.e., mRNA containing the Luc coding sequence, the subdomain II of the αAmy3 3'UTR, and the Nos 3'UTR) mRNAs decayed slowly in the presence of sucrose, but decayed rapidly in the absence of sucrose. In contrast, in the pLIN- and pLIIIN-transformed cells, the Luc-I-Nos, Luc-III-Nos mRNAs as well as the endogenous αAmy3 mRNA decayed rapidly in the presence of sucrose, but decayed slowly in the absence of sucrose. These results demonstrate that subdomains I and III, but not subdomain II, increase the stability of the Luc-Nos mRNA in response to sucrose starvation.

Figure 3:
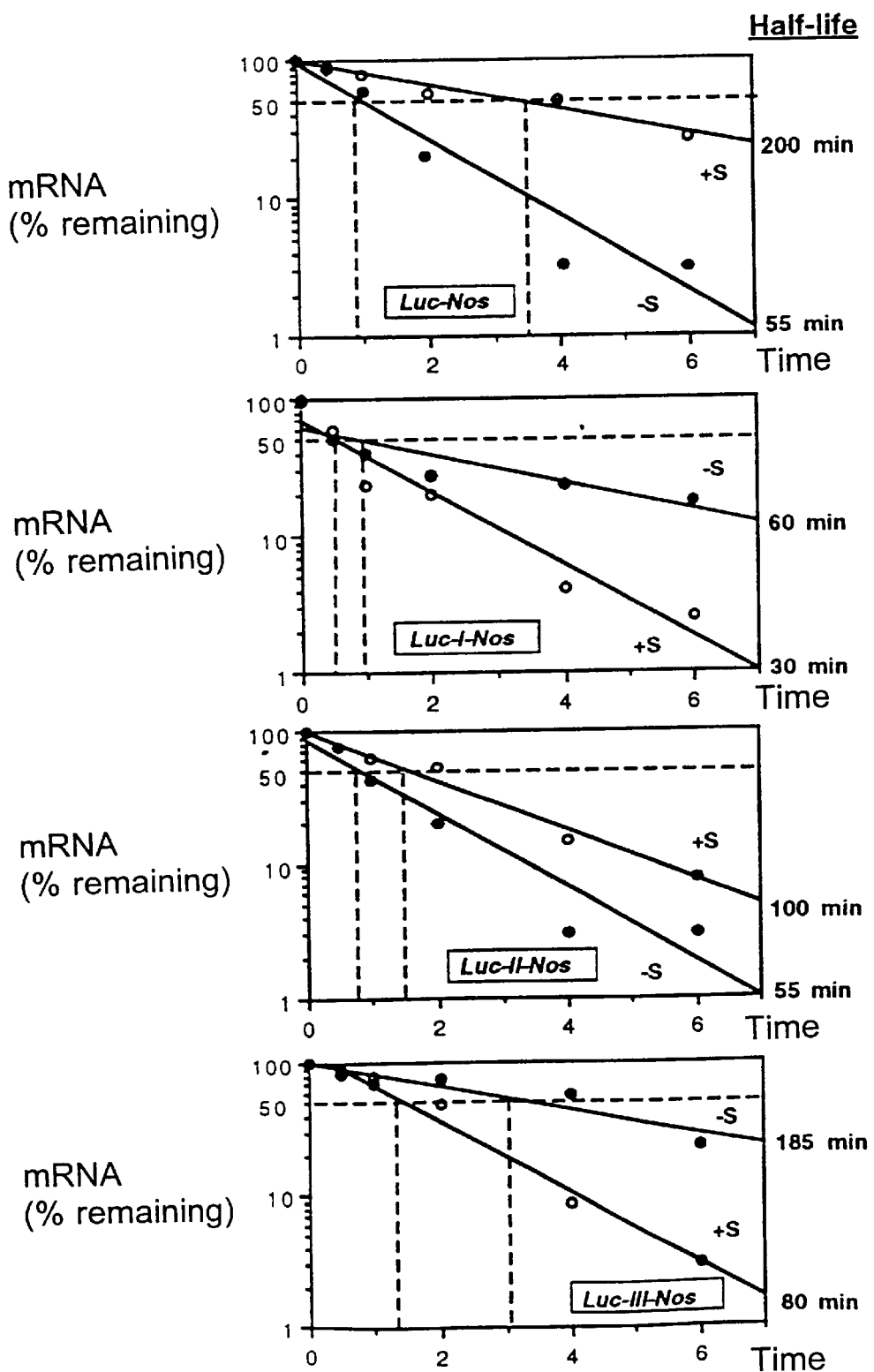
FIG. 3 is a set of graphs showing that various αAmy3 3' UTR fragments affect mRNA half-life in a sugar-responsive manner. The time on the horizontal axis is shown in hours. The open and filled circles indicate mRNA from cells grown in sugar-plus (+S) and sugar-minus (−S) medium, respectively. The dashed line indicates the time at which 50% of mRNA remained.

Half-lives of the above Luc mRNAs were determined and shown in FIG. 3. In the absence of sucrose, the half-life of the Luc-Nos mRNA was 55 min, which was similar to that of the Luc-I-Nos (60 min) and Luc-II-Nos (55 min) mRNA but 3.4-fold less than that of the Luc-III-Nos (185 min). In the presence of sucrose, the half-life of Luc-Nos mRNA was 200 min, which was 6.7-fold of the Luc-I-Nos mRNA (30 min), 2-fold of the Luc-II-Nos MRNA (100 min), and 2.5-fold of the Luc-III-Nos mRNA (80 min). These results suggest that in the absence of sucrose, fragment III delays the decay of the Luc-Nos mRNA. However, in the presence of sucrose, all three fragments promote the decay of the Luc-Nos mRNA.

EXAMPLE 2

In this example, the effects of various αAmy3 3' UTRs (i.e., various regions of the full-length αAmy3 3'UTR) on mRNA accumulation in rice protoplasts were examined with a highly sensitive method termed co-amplification reverse transcriptase-polymerase chain reaction (CRT-PCR). Unlike Northern or dot blot analysis, CRT-PCR allows simultaneous detecting and/or quantitation of multiple RNA transcript species. In this example, by "the αAmy3 3'UTR" is meant the full length αAmy3 3'UTR.

Plant Materials and Protoplast Isolation

Suspension cell cultures of rice (Oryzae sativa cv. Tainan 5) were propagated as described previously (Yu et al., *J. Biol. Chem.* 266:21131–21137, 1991). Protoplasts were isolated from rice suspension cells according to the methods described by Lee et al. (1989). For transfection, protoplast concentration was adjusted to $1 \times 10^7$ protoplasts/ml in KPR medium (Kao and Michayluk, 1975).

Plasmid Construction

Plasmid pαAmy3 was constructed using the pBluescript-KS(+) vector (Stratagene) and contains a 1.7-kb insert derived from a rice αAmy3 cDNA (Sheu et al., *J. Biol. Chem.*, 271:26998–27004, 1996). Plasmid pcRAc1.3 was constructed using the pBluescriptII-KS vector (McElroy et al., *Plant Mol. Biol.*, 14:163–171, 1990) and contains a 1.4-kb insert derived from a rice actin cDNA (Act1). These two plasmids were used as templates for PCR amplification of 3'UTRs.

All of the plasmids contain a maize ubiquitin gene (Ubi) promoter, a luciferase (Luc) or β-glucuronidase (Gus) coding sequence linked to the Ubi promoter, and a 3'UTR of the αAmy3, Act1, or Nos gene. To generate these plasmids, the PCR amplified 3'UTRs of αAmy3 and Act1 containing XbaI and SacII sites at two ends were first subcloned into pBluescriptII-KS(+), resulting in plasmids pMTC37 and pMTC39, respectively. The HindIII-BamHI DNA fragment containing the Ubi promoter, exon 1, intron 1, and part of exon 2 from pAHC18 (Bruce et al., *Proc. Natl. Acad. Sci.*, 86:9692–9696, 1989) was then inserted upstream of the αAmy3 3'UTR in pMTC 37 to generate plasmid pMTC24. To generate pMTC241, pMTC24 was linearized with KpnI and HIndIII, blunt-ended, and re-ligated to remove the multiple cloning sites. The Luc coding sequence was then excised from pAHC18 by BamHI and inserted into the same site between the Ubi promoter and the αAmy3 3'UTR in pMTC241 to generate plasmid pLAm. The Nos 3'UTR was excised from pAHC18 by BamHI and SacI. Then the plasmids pLAc and pLN were similarly constructed as was pLAm, except that they contained the Act1 and Nos 3'UTRs downstream of the Luc gene, respectively.

Figure 4:
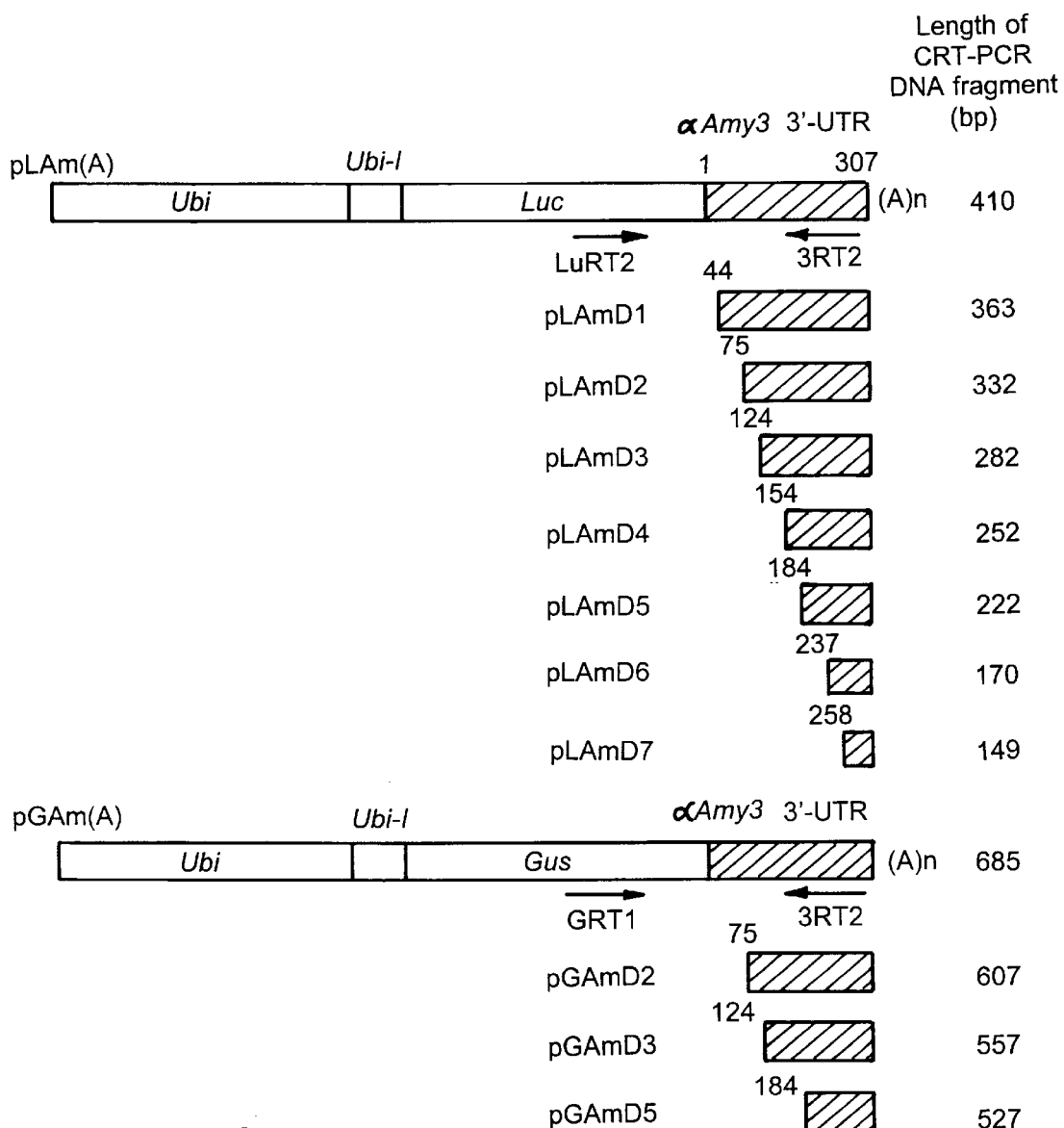
FIG. 4 is a set of schematic diagrams showing the structures of chimeric genes containing various 5' deletions of the full-length αAmy3 3'UTR. The nucleotide sequences are numbered from the first nucleotide after the translation stop codon TGA. Arrowheads indicate the positions of primers used for CRT-PCR. Expected sizes of the gene-specific DNA fragments generated by CRT-PCR are indicated in bp (base pairs).

To construct the plasmids containing serial deletions from the 5' end of the full-length αAmy3 3'UTR, pLAm was linearized at the KpnI and SpeI sites located between the Luc coding sequence and the αAmy3 3'UTR, and then subjected to Exonuclease III (Erase-a-Base kit, Promega) digestion at 15° C. for 2 min. Samples were taken at 30-second intervals. The resulting plasmid DNAs were amplified by PCR, using LuRT2 and 3RT2 (Table 1) as primers. PCR products were examined by electrophoresis on 6% nondenaturing polyacrylamide gel; and plasmids yielding the desired lengths of products, i.e., containing the desired 5'-deleted αAmy3 3'UTR, were selected. These plasmids were designated as pLAmD1 through pLAmD7 (FIG. 4). The exact deletion points were determined by DNA sequence analysis. The Luc coding sequence in pLAm, pLAmD2, pLAmD3, and pLAmD5 were replaced with Gus, generating plasmid pGAm, pGAmD2, pGAmD3, and pGAmD5.

tube and mixed with 5 μg of supercoiled plasmid DNA. If cotransfection was performed, 4 μg of test plasmid and 2 μg of reference plasmid were mixed and added. Subsequently, 10 μg of salmon sperm DNA, and 100 μl of F-medium (140 mM NaCl, 5 mM KCl, 0.75 mM $Na_2HPO_4$, 5 mM glucose, and 125 mM $CaCl_2.2H_2O$, pH 7.0) containing 40% (w/v) PEG (mol. wt. 8000, Sigma) were also added to the plasmid/cell mix. After incubation at room temperature for 20 min, 0.2 ml of DNA/cell mix was added into a well of a 24-well microculture plate. The well contained 2 ml of solidified 0.2% low melting temperature agarose (Gibco-BRL) in modified KPR medium. After 18 h of incubation, the protoplasts were transferred into a 1.5 ml Eppendorf tube and centrifuged for 5 seconds. The protoplasts were resuspended

TABLE 1

Oligonucleotides used in making 3' UTR constructs and in CRT-PCR analyses

| Name of primer | Region in a gene | Position in a gene | Nucleotide Sequence (5' → 3') | |
|---|---|---|---|---|
| 3-53 | 5' end of αAmy3 3'UTR | $-3-15^b$ | TAA TCTAGA TAGCGGGCTCAAGCCCTA XbaI | (SEQ ID NO:2) |
| 3RT2 | 3' end of αAmy3 3'UTR | $289-303^b$ | TCC CCGCGG TCAGTGAGTTTTTA SacII | (SEQ ID NO:3) |
| SP3 | 3' end of αAmy3 3'UTR | $248-263^b$ | TATATAATGTCAGGTT | (SEQ ID NO:4) |
| AS3 | 5' end of αAct1 3'UTR | $-3-12^b$ | TGC TCTAGA TAATTCTTCGACCCA XbaI | (SEQ ID NO:5) |
| A30 | 3' end of Act1 3' UTR | $228^{242b}$ | TCC CCGCGG TGGTACCCGCATCA SacII | (SEQ ID NO:6) |
| NosRT1 | 3' end of Nos 3' UTR | $168-180^b$ | GCGGGACTCTSSTCATAAAA | (SEQ ID NO:7) |
| 3RT1 | Coding region of αAmy3 | $1096-115^a$ | ACGGCATCAACGCCGGGAGC | (SEQ ID NO:8) |
| ART1 | Coding region of Act1 | $914-932^a$ | CTGATGGACAGGTTATCACC | (SEQ ID NO:9) |
| LuRT2 | Coding region of Gus | $1667-1686^a$ | TCAGCGATGACGAAATTCTT | (SEQ ID NO:10) |
| GRT1 | αAmy3 3'UTR | $1388-1407^a$ | TCTCTTTGATGTGCTGTGCC | (SEQ ID NO:11) |
| 3R1 | αAmy3 3'UTR | $3-17^b$ | TGAGCTC GGCTCAAGCCCTAAA SacI | (SEQ ID NO:12) |
| 3R2 | αAmy3 3'UTR | $121-135$ | TGAGCTC CTACAATCGGATACA SacI | (SEQ ID NO:13) |
| 3R3 | αAmy3 3'UTR | $120-134^b$ | TGAGCTC TTGTATCCGATTGTA SacI | (SEQ ID NO:14) |
| 3R4 | αAmy3 3'UTR | $185-199^b$ | TGAGCTC TGGCAAGCTACATAT SacZ | (SEQ ID ND:15) |
| 3R5 | αAmy3 3'UTR | $182-196^b$ | TGAGCTC GGCATATGTAGCTT SacI | (SEQ ID NO:16) |
| 3R6 | αAmy3 3'UTR | $252-266^b$ | TGAGCTC CCTGAACCTGAACCT SacI | (SEQ ID NO:17) | a. The first nucleotide of translation initiation codon ATG at +1
b. The firat nucleotide after translation stop codon as +1.

To construct plasmids containing other αAmy3 3'UTRs, DNA fragments encompassing the regions were first obtained by PCR, using pMTC37 as a template and pairs of oligonucleotides flanking these regions as primers (Table 1). Primers 3R1 and 3R2 were used to generate fragment I (i.e., subdomain I); primers 3R3 and 3R4 for fragment II (i.e., subdomain II); and primers 3R5 and 3R6 for fragment III (i.e., subdomain III). These fragments all contained, at both ends, a SacI site introduced by the PCR primers. The PCR products were hence digested with SacI and inserted into the same site between the Luc coding sequence and the Nos 3'UTR in pLN. Fragments I, II, and III were inserted into pLN in obverse orientation to generate pLIN, pLIIN, and pLIIIN, and in reverse orientation to generate pLIRN, pLIIRN, and pLIIIRN.

Polyethylene Glycol (PEG)—Mediated Transfection of Rice Protoplasts

The PEG-mediated transfection of rice protoplasts was performed by a method as described by Lyznik et al, (*Biotechniques*, 10:294–300, 1991), with modification. 100 μl of rice protoplasts were transferred to a 1.5-ml Eppendorf in 0.5 ml of modified KPR medium containing glucose or mannitol, transferred into a well of another 24-well microculture plate, and incubated for various lengths of time.

Primers

Primers for the coding regions of the αAmy3, Act1, Luc, or Gus gene, and for a 3'UTRs of αAmy3, Act1, or Nos gene were designed so that the molecular weight of the RT (reverse transcription)-PCR products for the various endogenous and transgene transcripts were different from each other and could be distinguished by agarose gel electrophoresis. Locations and nucleotide sequences of these primers are shown in FIGS. 1 and 4, and listed in Table 1.

Reverse Transcription-Polymerase Chain Reaction

Total RNA was extracted from protoplasts by the method of Verwoerd et al. (1989). Twenty μg of total RNA was incubated in a volume of 20 μl with 5 μM DTT, 2 units/μl RNasin (Promega), and 1 unit of RNase-free DNase I (Promega). After 15 min of incubation at 37° C., the RNA was incubated at 80° C. for 3 min and placed on ice. Reverse transcription of the RNA was performed in 20 μl of the reaction mix, which contained 50 mM Tris-HCl, pH 8.3, 75 mM KCl, and 3 mM $MgCl_2$, 10 μg of the RNA, 50 pmole oligo $(dT)_{18}$ primer, 5 mM DTT, 0.5 mM each dNTP, 2 units/μl RNasin, and 10 units/μl Maloney murine leukaemia virus reverse transcriptase (MMLV-RTase). The reaction was carried out at room temperature for 10 min, then at 37° C. for 1 h, and was terminated at 94° C. for 5 min. The RT product mix was used as a cDNA stock and could be stored at −70° C. for several months.

PCR was carried out in a volume of 50 μl containing 2.5 μl RT product mix prepared above, 10 mM Tris-HCl (pH 8.3), 50 mM KCl, 3 mM $MgCl_2$, 0.1 mM each dNTP, 100 pmole each primer, 10% DMSO, and 3 units super Taq DNA polymerase (Promega). Cycling was controlled by a programmable thermal cycler (Hybaid). Denaturation was at 94° C. for 1 min; primer annealing at 50° C. for 1.5 min; and primer extension at 72° C. for 2 min. The reaction was run for 30 cycles before a final 10 min of primer extension at 72° C. The RT-PCR products were fractionated in 2% agarose gel and visualized by ethidium bromide staining.

Primer Extension Analysis

Primer extension analysis was performed by a method essentially the same as described by (Sutliff et al., *Plant Mol. Biol.*, 16:579–591, 1991), except that 10 μg of total RNA was used as a template and the primer extension products were analyzed on 1% agarose gel.

Results (1) CRT-PCR: A method of Measuring Steady-State mRNA Levels of Individual Several Genes Simultaneously To define cis-acting sequences in the α-amylase mRNA that control gene expression in vivo, we sought to develop a method for measuring mRNA levels in rice protoplasts. CRT-PCR was chosen for this purpose, because it can measure individual steady-state mRNA levels of several genes simultaneously. The principle of CRT-PCR is illustrated in FIG. 1: At least two sets of gene-specific primers are included in the same RT-PCR reaction to amplify cDNAs from mRNAs of the genes of interest. Positions of the primers corresponding to individual genes are designed so as to produce DNA fragments of distinct sizes that are diagnostic for each mRNA. The relative intensity of the DNA bands obtained after electrophoresis and ethidium bromide staining correlate with the relative amounts of different mRNAs present in the sample, thus allowing simultaneous quantification of transcripts from different genes.

The validity of CRT-PCR was demonstrated in a reconstruction experiment. In this experiment, various amounts of mRNA purified from rice suspension cells cultured with or without glucose for 2 days were reverse transcribed; and the RT products were PCR-amplified, using 2 pairs of primers specific for the cDNAs of the Act1 and αAmy3 mRNAs (FIG. 1). Two PCR products were produced, one corresponding to the Act1 cDNA (640 bp) and the other to the αAmy3 cDNA (500 bp). As shown in ethidium bromide-stained agarose gel, the band intensities of both products decreased with reduced mRNA input. The band intensity of αAmy3 DNA was higher than that of Act1 DNA for all RNA samples from glucose-starved cells, and vice versa for all RNA samples from glucose-provided cells.

These results are consistent with the previous blot analysis of RNA from intact suspension cells (Sheu et al., *J. Biol. Chem.*, 271:26998–270041996). When the amounts of PCR products as shown in ethidium bromide-stained agarose gel were quantified and plotted against the amounts of input RNA used for CRT-PCR, a linear relationship was observed between the levels of the CRT-PCR products and the concentrations of input mRNAs. Thus, the relative amount of mRNA can be estimated from its CRT-PCR product.

(2) Effect of the αAmy3 3'UTR on mRNA Accumulation as Determined by CRT-PCR Analyses To determine whether the 3'UTR of αAmy3 functions as a determinant of mRNA stability in response to sugar availability, a series of constructs (FIG. 1) were prepared. Plasmids pLAm containing Ubi-Luc-αAmy3, pLAc containing Ubi-Luc-Act1, and pLN containing Ubi-Luc-Nos were transfected into rice protoplasts. The protoplasts were then incubated in a glucose-containing or glucose-free medium.

Glucose, instead of sucrose, was used as the carbon source here. The reason was that rice protoplasts contain no cell walls and hence no cell wall-bound invertase, which hydrolyzes sucrose into glucose and fructose before up-take by intact suspension cells (Yu et al., *J. Biol. Chem.*, 266:21131–21137, 1991), and that sucrose cannot be transported efficiently into protoplasts. It has been shown that glucose represses α-amylase gene expression as well as sucrose does (Yu et al., *J. Biol. Chem.*, 266:21131–21137, 1991).

Total RNA was purified from the protoplasts, and CRT-PCR was performed using multiple sets of primers which simultaneously amplified cDNAs derived from the endogenous Act1 and αAmy3 mRNAs, and from the foreign chimeric Luc-αAmy3, Luc-Act1, or Luc-Nos mRNAs (FIG. 1).

The data showed that, in both transfected and non-transfected protoplasts, accumulation of the endogenous Act1 mRNA was enhanced by glucose, and that of the αAmy3 mRNA was suppressed by glucose. This result indicates that expression of the endogenous Act1 and αAmy3 is subject to opposite regulation by glucose in protoplasts as well as in intact suspension cells (Sheu et al., *J. Biol. Chem* 271:26998–27004, 1996). Accumulation of the Luc-αAmy3 mRNA in pLAm-transfected protoplasts was also suppressed by glucose. In contrast, accumulation of the Luc-Act1 mRNA in pLAc-transfected protoplasts, and accumulation of the Luc-Nos mRNA in pLN-transfected protoplasts, were both enhanced by glucose. These results demonstrate that the αAmy3 3'UTR enhances, while the Act1 and Nos 3'UTRs reduce, accumulation of the Luc mRNA in glucose-starved cells.

In the above experiments, the expression of endogenous Act1 and αAmy3 was used as an internal control for indication of normal physiology in response to availability of glucose.

A reference gene can also be co-transfected with the test genes, with its expression used as an internal control. For instance, plasmid pGN containing Ubi-Gus-Nos was co-transfected with pLN or pLAm into rice protoplasts which were subsequently incubated in a medium with or without glucose. CRT-PCR was performed using primers that amplified cDNAs derived from the foreign chimeric Gus-Nos, Luc-Nos, or Luc-αAmy3 mRNAs (FIG. 1). The data showed that accumulation of the Gus-Nos mRNA, like that of the Luc-Nos mRNAs, was enhanced by glucose. In contrast, accumulation of the Luc-⊖Amy3 mRNA was repressed by glucose. This result further demonstrates that the αAmy3 3'UTR specifically enhances the accumulation of reporter mRNA in response to glucose starvation.

(3) Effect of the αAmy3 3'UTR on mRNA Accumulation as Determined by Primer Extension Analysis The effect of the αAmy3 3'UTR on mRNA accumulation was confirmed with another approach—primer extension analysis. Plasmids pLAm and pLAc were transfected into rice protoplasts which were then incubated in a medium with or without glucose. Total RNA was purified from the protoplasts and used as templates for primer extension analysis using primer 3RT2 or A30 (Table 1) that was also used in CRT-PCR analyses (FIG. 1). Levels of the extension products derived from the endogenous αAmy3 (1.7 kb) and the chimeric Luc-αAmy3 (2.1 kb) mRNAs in pLAm-transfected protoplasts were shown to be reduced by glucose. In contrast, levels of the extension products derived from the endogenous Act1 (1.4 kb) and the chimeric Luc-Act1 (2.1 kb) mRNAs in pLAc-transfected protoplasts were enhanced by glucose.

This result was consistent with that obtained with CRT-PCR, confirming that the αAmy3 3'UTR plays a role in the sugar-dependent repression of mRNA accumulation.

(4) Kinetics of Accumulation of mRNA Carrying the αAmy3 3'UTR in Protoplasts

To analyze the kinetics of accumulation of a reporter mRNA carrying the αAmy3 3'UTR, rice protoplasts were transfected with pLAm and then incubated for various lengths of time in a medium with or without glucose. CRT-PCR analysis showed that, within 2 days, levels of Act1 mRNA remained high in the presence of glucose, but decreased with time in the absence of glucose. In contrast, levels of both the endogenous αAmy3 and chimeric Luc-αAmy3 mRNAs were initially low in the presence of glucose, but increased significantly within 12 hr following glucose depletion. At day 2, levels of Act1 and αAmy3 mRNAs in transfected protoplasts in the presence or absence of glucose, respectively, were similar to those in non-transfected protoplasts. This result suggests that the sugar-dependent expression pattern of the foreign chimeric gene is similar to that of the endogenous gene.

Similar experiments were performed to define more precisely the time required for induction of Luc-αAmy3 mRNA accumulation by glucose depletion. Levels of both endogenous αAmy3 and chimeric Luc-αAmy3 mRNAs were found to increase significantly within 2 h after depletion of glucose, confirming that accumulation of the Luc mRNA carrying the αAmy3 3'UTR has the same kinetics as that of the endogenous αAmy3 mRNA.

(5) 5' Deletion Analysis of the αAmy3 3'UTR

To identify sequences in the αAmy3 3'UTR that determine the sugar-dependent instability of mRNA, a series of 5' deletions of the αAmy3 3'UTR were generated. The truncated αAmy3 3'UTRs were inserted downstream of the Ubi promoter-Luc coding region (FIG. 4). The resulting constructs were then transfected into rice protoplasts and their expression analyzed by CRT-PCR. CRT-PCR products were analyzed on agarose gel.

Accumulations of the endogenous Act1 mRNA were shown to be enhanced by glucose, and those of the αAmy3 mRNA were suppressed by glucose, in either transfected or non-transfected protoplasts. Accumulations of the wild type or mutant Luc-αAmy3 mRNA in protoplasts transfected with pLAm, pLAmD1, pLAmD2, pLAmD5, and pLAmD6 were suppressed by glucose. In contrast, accumulations of the mutant Luc-αAmy3 mRNA in protoplasts transfected with pLAmD3, pLAmD4, and pLAmD7 were enhanced by glucose. This result indicates that multiple regions in the αAmy3 3'UTR repress or de-repress the accumulation of Luc mRNA in a sugar-dependent manner.

To use a reference gene as an internal control, pGN was cotransfected with each of the wild type or mutant plasmids used in the experiments into the rice protoplasts. Accumulation of mRNAs determined by CRT-PCR was as expected.

To test whether the effect of deletion on mRNA accumulation changed with different coding sequences, three DNA fragments containing the deleted αAmy3 3'UTRs were chosen and fused downstream of the Ubi promoter-Gus coding region (FIG. 4). The resulting constructs were then cotransfected with pLN into rice protoplasts and their expression analyzed by CRT-PCR. Levels of the Luc-Nos mRNA were shown to be higher in the presence of glucose than in the absence of glucose. This result was consistent with the results in Part (2). Accumulations of the wild type or mutant Gus-αAmy3 mRNA in protoplasts transfected with pGAm, pGAmD2, and pGAmD5 were suppressed by glucose. In contrast, accumulation of the mutant Gus-αAmy3 mRNA in protoplasts transfected with pGAmD3 was enhanced by glucose. These results demonstrate that the sugar-dependent repression or derepression of mRNA accumulation controlled by multiple sequences in the αAmy3 3'UTR is independent of the connected coding sequences.

(6) Functional Analysis of the Multiple Sugar-Responsive Regions in the αAmy3 3'UTR As shown by the above deletional analysis, in the absence of glucose, the sequences in the αAmy3 3'UTR spanning nucleotides 1 to 124 and 184 to 258 were involved in enhancing mRNA accumulation, whereas the sequence spanning nucleotides 124 to 184 were involved in suppressing mRNA accumulation.

To investigate whether these regions by themselves can play the same roles, DNA fragments containing the αAmy3 3'UTR from sequences 3 to 135 (fragment I), 119 to 199 (fragment II), and 182 to 276 (fragment III) were amplified by PCR. These fragments were inserted between the Ubi promoter-Luc coding region and the Nos 3'UTR (FIG. 1) to generate pLIN, pLIIN, and pLIIIN, respectively (see also Example 1, supra). The resulting constructs were then cotransfected with pGN into rice protoplasts and their expression analyzed by CRT-PCR.

The CRT-PCR analysis showed that the Gus-Nos mRNA levels (internal control) were enhanced by glucose as expected, and the accumulation of the Luc-I-Nos or Luc-III-Nos MRNA in protoplasts containing PLIN or PLIIIN was suppressed by glucose. On the contrary, accumulation of the Luc-II-Nos mRNA in protoplasts transfected with pLIIN was enhanced by glucose.

Thus, the above analyses demonstrate that at least two regions (or subdomains) in the αAmy3 3'UTR could confer a sugar-dependent repression of accumulation of the Luc-Nos mRNA whose accumulation otherwise was enhanced by sugar. These results were consistent with those obtained by RNA dot blot analysis (see Example 1, supra, e.g., FIG. 21).

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. An expression vector comprising a promoter capable of directing expression of a coding sequence in an angiosperm cell, and a 3' untranslated region of a rice α-amylase gene, wherein, after the coding sequence is inserted into the vector, the 3' untranslated region and the coding sequence are transcribed into a single mRNA whereby the 3' untranslated region of the rice α-amylase gene increases stability of the mRNA.

2. The vector of claim 1, wherein said α-amylase gene is an αAmy3 gene.

3. The vector of claim 2, wherein said 3' untranslated region consists of 20 or more consecutive nucleotides from SEQ ID NO:1.

4. The vector of claim 1, further comprising a signal sequence encoding a signal peptide, wherein said signal sequence is situated downstream of said promoter.

5. The vector of claim 4, wherein said signal sequence is derived from an α-amylase gene.

6. The vector of claim 5, wherein said signal sequence is derived from a rice αAmy8 gene.

7. The vector of claim 4, wherein said α-amylase gene is an αAmy3 gene.

8. The vector of claim 7, wherein said 3' untranslated region consists of 20 or more consecutive nucleotides from SEQ ID NO:1.

9. A method of producing a polypeptide in an angiosperm cell, said method comprising:

providing an expression construct which comprises (i) a coding sequence for the polypeptide, (ii) a promoter capable of directing expression of the coding sequence in the angiosperm cell, and (iii) a 3' untranslated region of a rice α-amylase gene, wherein the coding sequence and the untranslated region are heterologous to each other and positioned for transcription into a single mRNA whereby the 3' untranslated region of the rice α-amylase gene increases stability of the mRNA;

transforming an angiosperm host cell with the expression construct; and subjecting the transformant host cell to a sugar-free environment to promote expression of the polypeptide.

10. The method of claim 9, wherein said α-amylase gene is an αAmy3 gene.

11. The method of claim 10, wherein the 3' untranslated region consists of 20 or more consecutive nucleotides of SEQ ID NO:1.

12. The method of claim 11, wherein the expression construct further comprises, between the promoter and the coding sequence, a signal sequence encoding a signal peptide.

13. The method of claim 12, wherein the signal sequence is derived from a rice αAmy8 gene.

14. A method of producing a polypeptide in an angiosperm cell, said method comprising:

providing an expression construct which comprises (i) a coding sequence for the polypeptide, (ii) a promoter capable of directing expression of the coding sequence in the angiosperm cell, and (iii) a 3' untranslated region of a rice α-amylase gene, wherein the coding sequence and the untranslated region are heterologous to each other and positioned for transcription into a single mRNA whereby the 3' untranslated region of the rice α-amylase gene increases stability of the mRNA;

transforming an angiosperm host cell with the construct; and subjecting the transformant host cell to a sugar-containing environment to promote expression of the polypeptide.

15. The method of claim 14, wherein said α-amylase gene is an αAmy3 gene.

16. The method of claim 15, wherein the 3' untranslated region consists of 20 or more consecutive nucleotides of SEQ ID NO:1.

17. The method of claim 16, wherein the expression construct further comprises, between the promoter and the coding sequence, a signal sequence encoding a signal peptide.

18. The method of claim 17, wherein the signal sequence is derived from a rice αAmy8 gene.

* * * * *